(12) United States Patent
Lyu et al.

(10) Patent No.: US 6,303,805 B1
(45) Date of Patent: Oct. 16, 2001

(54) METALLOCENE COMPLEXES AND METHOD OF PREPARING THE SAME

(75) Inventors: Yi-Yeol Lyu; Duck-Joo Yang; Keun-Byoung Yoon; Seok Chang, all of Taejeon; Won-Cheol Jung, Seoul, all of (KR)

(73) Assignee: Samsung General Chemical Co., Ltd. (KR)

( * ) Notice: Subject to any disclaimer, the term of this patent is extended or adjusted under 35 U.S.C. 154(b) by 0 days.

(21) Appl. No.: 09/392,442

(22) Filed: Sep. 9, 1999

(30) Foreign Application Priority Data

Dec. 3, 1998 (KR) .................................. 98-52822

(51) Int. Cl.⁷ .............................. C07F 17/00; C07F 7/00; B01J 31/00
(52) U.S. Cl. ........................... 556/52; 556/136; 556/137; 556/140; 556/146; 502/152; 526/160; 526/943
(58) Field of Search .............................. 556/52, 137, 140, 556/146, 136; 502/152; 526/160, 943

(56) References Cited

U.S. PATENT DOCUMENTS

| | | | |
|---|---|---|---|
| 5,233,093 | 8/1993 | Pitchai et al. | 568/454 |
| 5,567,847 | 10/1996 | Vedage et al. | 564/493 |

OTHER PUBLICATIONS

Dyker, G., "A survey of reaction conditions for palladium–catalyzed processes," *Organometallic Chem.*, 1998, 555, 141–143.

Mansour, M.A. et al., "Linear Chain Au(I) Dimer Compounds as Environmental Sensors: A Luminescent Switch for the Detection of Volatile Organic Compounds," *J. Am. Chem. Soc.*, 1998, 120, 1329–1330.

Vickery, J.C. et al., "Solvent–Stimulated Luminescence from the Supramolecular Aggregation of a Trinuclear Gold(I) Complex that Displays Extensive Intermolecular Au···Au Interactions," *Angew. Chem. Int. Ed. Engl.*, 1997, 36(11), 1179–1181.

*Primary Examiner*—Porfirio Nazario-Gonzalez
(74) *Attorney, Agent, or Firm*—Woodcock Washburn Kurtz Mackiewicz & Norris LLP

(57) ABSTRACT

The metallocene complexes according to the present invention are prepared by reacting a transition metal complex of Group III-X of the Periodic Table, having at least one cycloalkanedienyl group, with a compound having at least two functional groups. The transition metal complex has a main ligand such as a cycloalkanedienyl group and at least one ancillary ligand which coordinated to a transition metal of Group III-X. The functional groups in the compound having at least two functional group are selected from the group consisting of a hydroxyl group (—OH), a thiol group (—SH), a primary amine group (—NH$_2$), a secondary amine group (RNH—), a tertiary amine group (RR'N) a primary phosphorous group (—PH$_2$), a secondary phosphorous group (RPH—), a tertiary phosphorous group (RR'P), a thiirane group

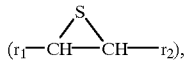

$(r_1$—CH—CH—$r_2)$, etc.

19 Claims, No Drawings

METALLOCENE COMPLEXES AND METHOD OF PREPARING THE SAME

FIELD OF THE INVENTION

The present invention relates to metallocene complexes. More specifically, the present invention relates to new metallocene complexes with high selectivity and activity, which are prepared by reacting a transition metal complex of Group IIIB-VIII of the Periodic Table, having at least one cycloalkanedienyl group, with a compound having at least two functional groups.

BACKGROUND OF THE INVENTION

A binuclear metallocene complex bridged by a functional group shows excellent properties as a catalyst (M. A. Mansour et al. at *J. Am. Chem. Soc.* 1998, 120, 1329–1330; and J. C. Vickery et al. *Angew. Chem. Int. Ed. Engl.* 1997. 36, 1179–1181). Also, it was found that a dimeric palladium compound bridged by a functional group has excellent activity than a palladium acetate compound in the Heck reaction (G. Dyker at Journal of Organometallic Chemistry 1998. 555 141–143).

U.S. Pat. No. 5,233,093 discloses an improved allyl alcohol hydroformylation process and a catalyst therefor. The process employes a catalyst system comprising a Group VIII metal carbonyl complex catalyst, a trisubstituted phosphine, a neutral Group VIII(a) metal complex co-catalyst, and optionally, a diphosphinoalkane. The bimetallic catalyst systems give high selectivity.

U.S. Pat. No. 5,567,847 discloses a process for the production of amines by the catalytic disproportionation of a feedstock containing a primary amine to produce a reaction product containing a secondary amine. The patent resides in the use of a bimetallic catalyst comprising nickel or cobalt in combination with rhodium, palladium, ruthenium or platinum.

Korean Patent Application No. 98-21032 discloses new catalysts having at least two cycloalkanedienyl groups, which are synthesized by bridging metallocene moleculars with an ancillary ligand having at least two functional groups. The catalysts have higher activity than conventional catalysts.

The present inventors have developed a method of preparing new metallocene complexes with high activity, such as bimetallic complex, trimetallic complex, tetrametallic complex, etc. The method of preparing the metallocene catalysts comprises reacting a compound having at least two functional groups with a metal compound of Group IIIB-VIII of the Periodic Table having at least one cycloalkanedienyl group.

OBJECTS OF THE INVENTION

An object of the present invention is to provide metallocene complexes in which two metallocene complexes are bridged with an ancillary ligand, which are prepared by reacting a compound having at least two functional groups with transition metal complexes of Group IIIB-VIII having at least one cycloalkanedienyl group.

Another object of the present invention is to provide metallocene complexes having high selectivity and activity.

A further object of the present invention is to provide metallocene complexes with high activity which are capable of preparing polyolefin or polystyrene having good stereoregularity, high melting temperature and good molecular weight distribution.

A further object of the present invention is to provide metallocene complexes with high activity which are capable of preparing a large amount of polyolefin or polystyrene by using small amount of a co-catalyst.

A further object of the present invention is to provide methods of reparing the metallocene complexes above and methods of polymerizing olefin or styrene by using the metallocene complexes.

These and other objects and advantages of this invention will be apparent from the ensuing disclosure and appended claims.

SUMMARY OF THE INVENTION

The metallocene complexes according to the present invention are prepared by reacting a transition metal complex of Group IIIB-VIII of the Periodic Table, having at least one cycloalkanedienyl group, with a compound having at least two functional groups. The transition metal complex has at least one main ligand such as a cycloalkanedienyl group and at least one ancillary ligand which are coordinated with a transition metal of Group IIIB-VIII. The functional groups in the compound having at least two functional groups are selected from the group consisting of a hydroxyl group (—OH), a thiol group (—SH), a primary amine group (—NH$_2$), a secondary amine group (RNH—), a tertiary amine group (RR'N) a primary phosphorous group (—PH$_2$), a secondary phosphorous group (RPH—), a tertiary phosphorous group (RR'P), a thiirane group

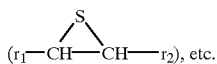

$(r_1$—CH—CH—$r_2)$, etc.

Also, the metallocene complexes of the present invention can be prepared by reacting a transition metal complex (a half metallocene complex) with a dianion, a trianion or a tetraanion complex. The dianion, trianion or tetraanion complex is produced by reacting a compound having a hydroxyl group (—OH), a thiol group (—SH), a primary amine group (—NH$_2$), a secondary amine group (—NH—), a primary phosphorous group (—PH$_2$) or a secondary phosphorous group (RPH—) with an alkali metal compound.

DETAILED DESCRIPTION OF THE INVENTION

The metallocene complexes of the present invention have a structure in which ancillary ligands of a transition metal complex (a half metallocene complex) are bridged with a functional group of a compound having at least two functional groups. The metallocene complexes of the present invention can be prepared in various chemical structures depending on the types of the transition metal complex (half metallocene complex) and the compound having at least two functional groups, and the molar ratio of the reactants.

The metallocene complexes of the present invention are prepared by reacting a transition metal complex represented by the following formula (A) with a compound having two, three or four functional groups represented by the following formula (B), (C) and (D), respectively. The transition metal complex contains at least one cyclopentadienyl group. The metallocene complexes have a structure in which ancillary ligands of a transition metal complex are bridged with a functional group of a compound having at least two functional groups.

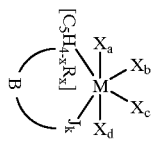
(A)

$T^1-Y-R^2-Y^1-T^2$ (B)

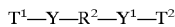 (C)

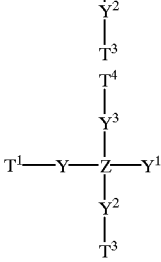 (D)

wherein
- M is a transition metal of Group IIIB-VIII of the Periodic Table;
- R is a hydrocarbon group of $C_1$~$C_{20}$ or a hydrocarbon group of $C_1$~$C_{20}$ containing a halogen, an amine group, a phosphine group or an alkoxy group, and the two adjacent R groups are bonded to a carbon of a hydrocarbon group $C_4$~$C_{20}$ to form a polycycliccyclopentadienyl group in the transition metal complex;
- x is 0, 1, 2, 3 or 4;
- B is a covalent bonding group linking $(C_5H_{4-x}R_x)$ and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;
- J is selected from the group consisting of a cyclopentadienyl group, an alkyl substituted amine group, an aryl substituted amine group, an alkyl substituted phosphine group, an aryl substituted phosphine group, a sulfur atom and an oxygen atom;
- k is 0 or 1, and when k is 0, B is a hydrogen atom or a methyl group;
- X is selected from the group consisting of a halogen, a triflate, a trifluoroacetate, a hydroxy, an alkyl substituted siloxy, an aryl substituted siloxy, a triphenylphosphine, an alkyl, and an aryl;
- a, b, c and d are 0 or 1;
- $T^1$, $T^2$, $T^3$ and $T^4$ are selected from the group consisting of H, Na, Li, K, and MgX (magnesium halide);
- Y, $Y^1$, $Y^2$ and $Y^3$ are selected from the group consisting of an oxygen atom, a sulfur atom, an alkyl with or without a double bond or a hetero atom, an aryl with or without a double bond or a hetero atom, a thiirane group

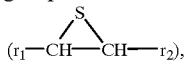

—$Nr_1$ and —$Pr_2$, wherein $r_1$ and $r_2$ are selected from the group consisting of a hydrogen atom, an alkyl group of $C_1$~$C_{10}$, a cycloalkyl group of $C_1$–$C_{10}$, an alkoxy group of $C_1$~$C_{10}$, an aryl group of $C_6$~$C_{20}$, an alkylaryl group of $C_6$~$C_{20}$ and an arylalkyl of $C_6$~$C_{20}$;
- $R^2$ is selected from the group consisting of a linear or branched alkyl group of $C_1$~$C_{20}$; a cycloalkyl group of $C_3$~$C_{20}$; a substituted cycloalkyl group of $C_3$~$C_{20}$; an aryl group of $C_6$~$C_{40}$; and an alkyl group, an aryl group, an alkylaryl group and an arylalkyl group either with or without a double bond or a hetero atom;
- Q is a nitrogen atom or —$Cr^3$, wherein $r^3$ is selected from the group consisting of a hydrogen atom, an alkyl group of $C_1$~$C_{10}$, a cycloalkyl group of $C_1$~$C_{10}$, an alkoxy group of $C_1$~$C_{10}$, an aryl group of $C_6$~$C_{20}$, an alkylaryl group of $C_6$~$C_{20}$ and an arylalkyl group of $C_6$~$C_{20}$; and
- Z is a carbon atom, a silicon atom, a germanium atom or

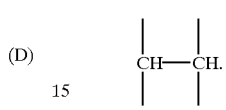

The transition metal complexes for preparing the metallocene complexes of the present invention are easily synthesized by using a commercially known method. The metallocene complexes of the present invention are prepared by reacting a transition metal complex (a half metallocene complex) of the formula (A) with a compound having at least two functional groups which will be normally two, three or four. The metallocene complexes are prepared by dissolving a transition metal complex (a half metallocene complex) of the formula (A) in a solvent, and then adding a compound having at least two functional groups of the formulae (B), (C) or (D) to the solution. The solvents used in the process above are, for example, THF, toluene, dichloromethane, hexane, heptane, benzene, ether, xylene, chloroform, mesitylene, etc. which are well known in the art. After stirring the mixed solution for a predetermined period of time, a metallocene complex of the present invention is obtained by removing the solvent under a reduced pressure. The reaction of the transition metal complex (A) and the compounds (B), (C) or (D) having at least two functional groups is carried out at the temperature of −78° C. to 118° C.

The representative examples of the metallocene complexes prepared in accordance with the present invention are represented as the following formula (I)~(VI):

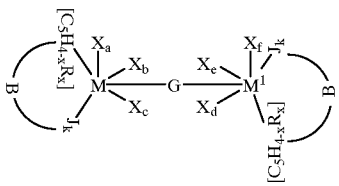 (I)

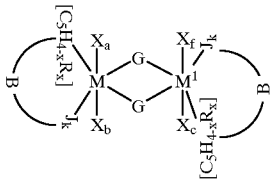 (II)

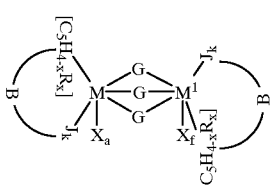 (III)

-continued

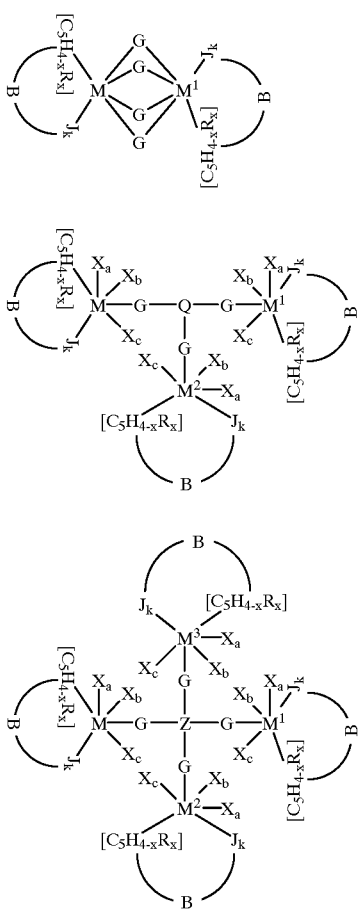

wherein

M, R, x, B, J, k, X, a, b, c, d, Q, and Z are the same as defined above;

$M^1$, $M^2$ and $M^3$ are the same as M;

a, b, c, d, e and f are 0 or 1; and

G is a bridging group which bonds two transition metal atoms, and represented as $-YR^2Y^1-$, wherein Y and $Y^1$ are selected from the group consisting of an oxygen atom, a sulfur atom, an alkyl group with or without a double bond or a hetero atom, an aryl group with or without a double bond or a hetero atom, a thiirane group

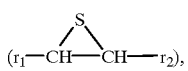

$-Nr^1$ and $-Pr^2$ (wherein $r_1$ and $r_2$ are a hydrogen atom, an alkyl group of $C_{1-10}$, a cycloalkyl group of $C_{1-10}$, lo, an alkoxy group of $C_{1-10}$, an aryl group of $C_{6-20}$, an alkylaryl group of $C_{6-20}$, or arylalkyl group of $C_{6-20}$), and $R^2$ is selected from the group consisting of a linear or branched alkyl group of $C_{1-20}$, a cycloalkyl group of $C_{3-20}$, a substituted cycloalkyl group of $C_{3-20}$, an aryl group of $C_{6-40}$, an alkyl group with or without a double bond or a hetero atom, an aryl group with or without a double bond or a hetero atom, an alkylaryl group with or without a double bond or a hetero atom, and an arylalkyl group with or without a double bond or a hetero atom.

The metallocene complex represented by the formula (I) above is prepared by reacting a transition metal complex (a half metallocene complex) represented by the formula (A) with a compound having two functional groups represented by the formula (B) in the molar ratio of 2:1.

The metallocene complex represented by the formula (II) above is prepared by reacting a transition metal complex (a half metallocene complex) represented by the formula (A) with a compound having two functional groups represented by the formula (B) in the molar ratio of 2:2.

The metallocene complex represented by the formula (III) above is prepared by reacting a transition metal complex (a half metallocene complex) represented by the formula (A) with a compound having two functional groups represented by the formula (B) in the molar ratio of 2:3.

The metallocene complex represented by the formula (IV) above is prepared by reacting a transition metal complex (a half metallocene complex) represented by the formula (A) with a compound having two functional groups represented by the formula (B) in the molar ratio of 2:4.

Also, the metallocene complex represented by the formula (V) above is prepared by reacting a transition metal complex (a half metallocene complex) represented by the formula (A) with a compound having three functional groups represented by the formula (C) in the molar ratio of 3:1. The compound of formula (C) has three functional groups.

Further, the metallocene complex represented by the formula (VI) above is prepared by reacting a transition metal complex (a half metallocene complex) represented by the formula (A) and a compound having four functional groups represented by the formula (D) in the molar ratio of 4:1. The compound of formula (C) has four functional groups.

Also, the metallocene complexes of the present invention can be prepared by reacting a transition compound (a half metallocene complex) with a dianion, a trianion or a tetraanion compound. The dianion, trianion or tetraanion compound is produced by reacting a compound having a hydroxyl group (—OH), a thiol group (—SH), a primary amine group ($-NH_2$), a secondary amine group (—NH—), a primary phosphorous group ($-PH_2$) or a secondary phosphorous group (RPH—) with an alkali metal compound.

The metallocene complexes prepared in the present invention can be used as a catalyst compound to polymerize styrene and olefin such as ethylene and propylene.

The present invention may be better understood by reference to the following examples which are intended for purposes of illustration and are not to be confined as in any way limiting the scope of the present invention, which is defined in the claims appended hereto.

EXAMPLES

Dimeric, trimeric and tetrameric metallocene complexes according to the present invention were prepared from transition metal complexes (half metallocene complexes) ($A_1$ through $A_{13}$) as shown in Table 1. Dimeric, trimeric and tetrameric metallocene complexes, $P_1-P_{13}$, according to the present invention were prepared from transition metal complexes (half metallocene complex), $A_1-A_{13}$, respectively. The process conditions for preparation of the dimeric, trimeric and tetrameric compounds, $P_1-P_{13}$, were shown in Table 2.

TABLE 1
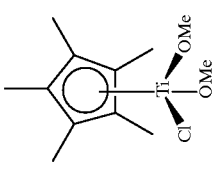

TABLE 1-continued
Metallocene Catalyst Complexes ($P_1$–$P_{13}$) / transition metal complexes ($A_1$–$A_{13}$)
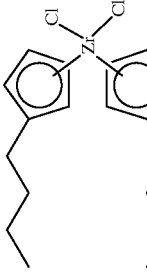

TABLE 1-continued
Metallocene Catalyst Complexes (P₁–P₁₃) / transition metal complexs (A₁–A₁₃)
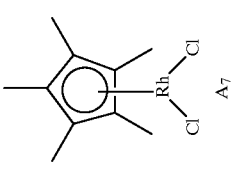

TABLE 1-continued

Metallocene Catalyst Complexes
($P_1$–$P_{13}$)

transition metal complexs
($A_1$–$A_{13}$)

TABLE 1-continued
Metallocene Catalyst Complexes ($P_1$–$P_{13}$)
transition metal complexs ($A_1$–$A_{13}$)
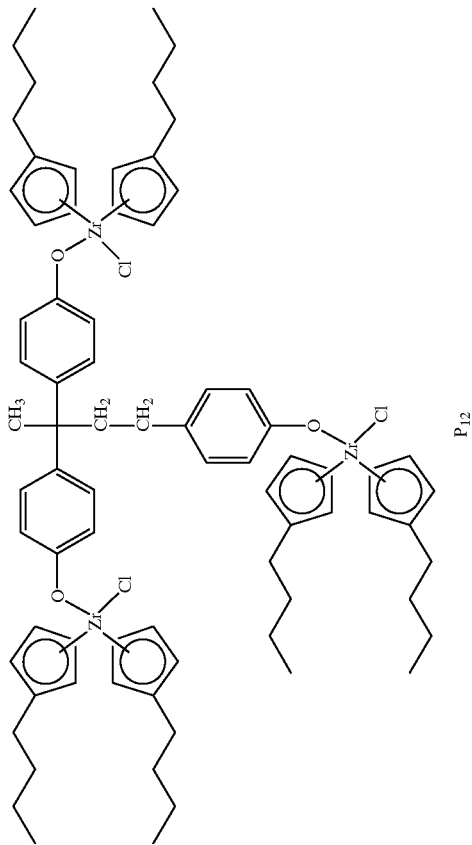
$P_{12}$
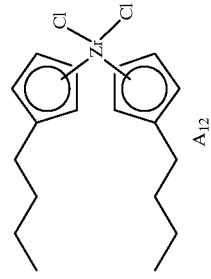
$A_{12}$ TABLE 1-continued

| transition metal complexs (A₁–A₁₃) | Metallocene Catalyst Complexes (P₁–P₁₃) |
|---|---|
| A₁₃ | P₁₃ |

Example 1

Compound ($A_1$) of 2.8 g in Table 1 was dissolved in THF of 100 ml, and to the solution was added a THF solution of 100 ml at −78° C. in which 1,10-hexanediol of 0.591 g and triethylamine of 1.11 g were dissolved. After the temperature of the resulting solution was increased to room temperature, the solution was stirred at room temperature for 12 hours, and the THF solvent was removed under a reduced pressure. Dimeric metallocene complex ($P_1$) of Table 1 was obtained with the yield of 78%. The process conditions were summarized in Table 2.

Example 2

Compound ($A_2$) of 2.85 g in Table 1 was dissolved in THF of 100 ml, and to the solution was added a THF solution of 100 ml at −78° C. in which 1,10-decanediol of 1.743 g and triethylamine of 2.22 g were dissolved. After the temperature of the resulting solution was increased to 45° C., the solution was stirred at room temperature for 12 hours, and the THF solvent was removed under a reduced pressure. Dimeric metallocene complex ($P_2$) of Table 1 was obtained with the yield of 65%. The process conditions were summarized in Table 2.

Example 3

Pentamethylcyclopentadienyltitaniumtrichloride ($A_3$) of 2.85 g was dissolved in toluene of 100 ml, and to the solution was added a toluene solution of 100 ml at −78° C. in which bisphenol A of 6.849 g and triethylamine of 3.33 g were dissolved. After the temperature of the resulting solution was increased to room temperature, the solution was stirred at room temperature for 15 hours, and then the toluene solvent was removed under a reduced pressure. Dimeric metallocene complex ($P_3$) of Table 1 was obtained with the yield of 65%. The process conditions were summarized in Table 2.

Example 4

Bis-n-butylcyclopentadienylzirconiumdichloride ($A_4$) of 0.2 g in Table 1 was dissolved in toluene of 100 ml, and to the solution was added at room temperature a toluene solution of 50 ml in which bisphenol A of 0.057 g and triethylamine of 0.6 ml were dissolved. After stirring the resulting solution at room temperature for 12 hours, and the toluene solvent was removed under a reduced pressure. Dimeric metallocene complex ($P_4$) of Table 1 was obtained with the yield of 90%. The process conditions were summarized in Table 2.

Example 5

Bis(cyclopentadienyl)hafniumdichloride ($A_5$) of 190 mg in Table 1 was dissolved in dichloromethane of 20 ml, and to the solution was added at room temperature for 2 minutes a methylenechloride solution of 5 ml in which bisphenol A of 58 mg and triethylamine of 0.11 ml were dissolved. After stirring the resulting solution at room temperature for 12 hours, and the methylenechloride solvent was removed under a reduced pressure. Dimeric metallocene complex ($P_5$) of Table 1 was obtained with the yield of 80%. The process conditions were summarized in Table 2.

Example 6

Pentamethylcyclopentadienyltantalumtetrachloride ($A_6$) of 229 mg in Table 1 was dissolved in dichloromethane of 20 ml, and to the solution was added at −78° C. a dichloromethane solution in which bisphenol A of 251 mg and triethylamine of 0.44 ml were dissolved. After heating the resulting solution to room temperature, the solution was stirred at the temperature for 12 hours, and then a dichloromethane solvent was removed under a reduced pressure. Dimeric metallocene complex ($P_6$) of Table 1 was obtained with the yield of 80%. The process conditions were summarized in Table 2.

Example 7

Pentamethylcyclopentadienylrhodiumdichloride ($A_7$) of 618 mg in Table 1 and 1,3-bis(diphenylphosphino)propane of 420 mg were put into a flask, and dichloromethane of 150 ml was added to the flask. The reaction was carried out at room temperature for about 15 hours. The solvent was removed under vacuum, and the obtained solid was filtered using hexane of about 50 ml. Orange colored dimeric metallocene complex ($P_7$) of Table 1 was obtained with the yield of 98%. The process conditions were summarized in Table 2.

Example 8

Pentamethylcyclopentadienyliridum of chloride ($A_8$) of 398.2 mg in Table 1 and 1,3-bis(diphenylphosphino)propane of 210 mg were put into a flask, and dichloromethane of 100 ml was added to the flask. The reaction was carried out at room temperature for about 15 hours. The solvent was removed under vacuum, and the obtained solid was filtered using hexane of about 50 ml. Red-colored dimeric metallocene complex ($P_8$) of Table 1 was obtained with the yield of 98%. The process conditions were summarized in Table 2.

Example 9

A toluene solution of 100 ml in which bisphenol A of 242 mg was dissolved was added to another toluene solution of 100 ml in which pentamethylcyclopentadienylnickeltriphenylphosphinomethane ($A_9$) of 500 mg in Table 1 was dissolved. The resulting solution was stirred at 70° C. for 2 days. Dimeric metallocene complex ($P_9$) of Table 1 was obtained with the yield of 50%. The process conditions were summarized in Table 2.

Example 10

Tetrametalcyclopentadienyldimethylsilyl(t-butylamino)titaniumdichloride ($A_{10}$) of 0.3 g in Table 1 was dissolved in dichloromethane of 100 ml, and to the solution was added at room temperature a dichloromethane solution of 50 ml in which bisphenol A of 0.185 g and triethylamine of 50 ml were dissolved. After stirring the resulting solution at room temperature for 24 hours, and the dichloromethane solvent was removed under a reduced pressure. Dimeric metallocene complex ($P_{10}$) of Table 1 was obtained with the yield of 70%. The process conditions were summarized in Table 2.

Example 11

Chlorocyclopentadienylbis(triphenylphosphine)ruthenium ($A_{11}$) of 96 mg in Table 1 was dissolved in dichloromethane of 12 ml, and to the solution was added at room temperature a dichloromethane solution of 20 ml in which silvertriflate of 35 mg was dissolved. After stirring the resulting solution at room temperature for 2 hours, the dichloromethane solution was filtered to remove the silverchloride. Dichloromethane solution of 5 ml in which 1,2,7,8-dithioepoxyoxtane of 11.6 mg was dissolved was added at room temperature to the solution in which the silverchloride was removed. After stirring the resulting solution for 1 hour, the solvent was reduced to 20 ml. A pentane of 20 ml was added therein to extract solid contents. The extracted solids were filtered and dried. Light yellow dimeric metallocene complex ($P_{11}$) was obtained with the yield of 85%. The process conditions were summarized in Table 2.

Example 12

(n-BuCp)$_2$ZrCl$_2$ (bis(n-butylcyclopentadienyl) zirconium dichloride) of 0.3 mmol was put into a flask, and to the flask was added toluene of 50 ml. The temperature of a reactor was kept at −78° C. Triol(α, α, α-tris(4-hydroxyphenyl)-1-ethyl-4-isopropylbenzene) of 0.1 mmol was put into a flask, and to the flask was added toluene of 50 ml, and then added triethylamine of 0.4 mmol (0.4 ml) with a syringe. The resulting solution was slowly added to a solution in which (n-BuCp)$_2$ZrCl$_2$ was dissolved in toluene. After the completion of addition, the reactor was slowly heated to room temperature. The reaction was carried out at room temperature for 12 hours. The resulting solution was filtered and a colorless solution was obtained. The toluene was removed under reduced pressure. Trimetallic compound ($P_{12}$) by bonding with triol was obtained with the yield of 88%. The process conditions were summarized in Table 2.

Example 13

Compound, $P_{13}$, was prepared in the same method as in Example 1 except for using tetraol of ¼ equivalent to Cp*Ti(OCH$_3$)$_2$ of 1 equivalent instead of 1,6-hexanediol. The tetraol was prepared by reacting tetraphenylolethane glycidyl ether with methylmagnesiumbromide of 4 equivalents. Compound, $P_{13}$, was obtained with the yield of 40%. The process conditions were summarized in Table 2.

TABLE 2

| Ex. | (A) | (P) | metal | compound having two functional groups(bridge) | solvent | temp(° C.) | hours | yield(%) |
|---|---|---|---|---|---|---|---|---|
| 1 | $A_1$ | $P_1$ | Ti | 1,6-hexanediol | THF | −78 → r.t. | 12 | 78 |
| 2 | $A_2$ | $P_2$ | Ti | 1,10-decanediol | THF | −78 → 45 | 12 | 65 |
| 3 | $A_3$ | $P_3$ | Ti | bisphenol A | toluene | −78 → r.t. | 15 | 82 |
| 4 | $A_4$ | $P_4$ | Zr | bisphenol A | toluene | r.t. | 12 | 90 |
| 5 | $A_5$ | $P_5$ | Hf | bisphenol A | CH$_2$Cl$_2$ | r.t. | 12 | 80 |
| 6 | $A_6$ | $P_6$ | Ta | bisphenol A | CH$_2$Cl$_2$ | −78 → r.t. | 12 | 80 |
| 7 | $A_7$ | $P_7$ | Rh | 1,3-bis(diphenylphos-phino)propane | CH$_2$Cl$_2$ | r.t. | 15 | 98 |
| 8 | $A_8$ | $P_8$ | Ir | 1,3-bis(diphenylphos-phino)propane | CH$_2$Cl$_2$ | r.t. | 15 | 98 |
| 9 | $A_9$ | $P_9$ | Ni | bisphenol A | toluene | 70 | 48 | 50 |
| 10 | $A_{10}$ | $P_{10}$ | Ti | bisphenol A | CH$_2$Cl$_2$ | r.t. | 24 | 70 |
| 11 | $A_{11}$ | $P_{11}$ | Ru | 1,2,7,8-ditioepoxy octane | CH$_2$Cl$_2$ | r.t. | 2 | 85 |
| 12 | $A_{12}$ | $P_{12}$ | Zr | α,α,α-tris(4-hydroxyphenyl)-1-ethyl-4-isopropylbenzene | toluene | −78 → r.t. | 12 | 88 |
| 13 | $A_{13}$ | $P_{13}$ | Ti | tetraphenylolethanegl | THF | −78 → r.t. | 12 | 40 | note)
r.t.: room temperature

Examples 14–26
Polymerization of Styrene and Ethylene

For measuring activities of metallocene complexes prepared in the examples, styrene and ethylene were polymerized as the following Examples 14–26. The polymerization conditions and the activities of the metallocene complexes were shown in Table 3.

TABLE 3

| Ex. | monomer | catalyst | solvent | amount of compound(μmol) | Ai/Ti | temp. | hours | (psi) | activity |
|---|---|---|---|---|---|---|---|---|---|
| 14 | styrene | * | toluene | 4 | 250 | 70° C. | 0.5 | 14.7 | 18,905 |
| 15 | styrene | $P_1$ | toluene | 4 | 250 | 70° C. | 0.5 | 14.7 | 22,342 |
| 16 | styrene | $P_2$ | toluene | 4 | 250 | 70° C. | 0.5 | 14.7 | 23,029 |
| 17 | styrene | $P_3$ | toluene | 4 | 250 | 70° C. | 0.5 | 14.7 | 32,195 |
| 18 | ethylene | $A_4$ | hexane | 2 | 25 | 80° C. | 1 | 115 | 11.5 |
| 19 | ethylene | $A_4$ | hexane | 2 | 50 | 80° C. | 1 | 115 | 29.0 |
| 20 | ethylene | $A_4$ | hexane | 2 | 75 | 80° C. | 1 | 115 | 30.0 |
| 21 | ethylene | $P_4$ | hexane | 2 | 25 | 80° C. | 1 | 115 | 16.0 |
| 22 | ethylene | $P_4$ | hexane | 2 | 50 | 80° C. | 1 | 115 | 32.0 |
| 23 | ethylene | $P_4$ | hexane | 2 | 75 | 80° C. | 1 | 115 | 37.0 |
| 24 | ethylene | ** | hexane | 2 | 25 | 80° C. | 1 | 115 | 12.5 |
| 25 | ethylene | ** | hexane | 2 | 50 | 80° C. | 1 | 115 | 27.0 |
| 26 | ethylene | ** | hexane | 2 | 75 | 80° C. | 1 | 115 | 32.0 | note)
*The catalyst compound used in Example 14 is represented as the following formula:

TABLE 3-continued

| Ex. | monomer | catalyst | solvent | amount of compound(μmol) | Ai/Ti | temp. | hours | (psi) | activity |
|---|---|---|---|---|---|---|---|---|---|

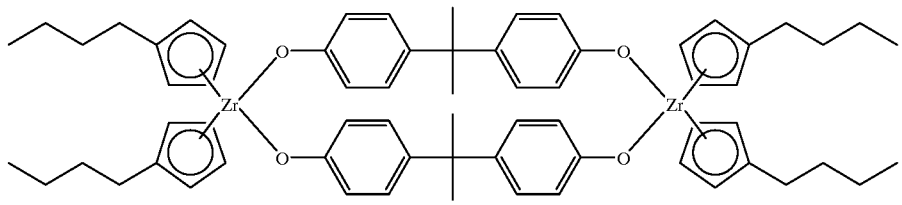

**The catalyst compound used in Example 24–26 is represented as the following formula:

Examples 14–17 were to prepare syndiotactic polystyrenes, and the units of activity thereof was kg·PS/[Ti]·[St]·h. Example 18–26 were to prepare polyethylenes, and the units of activity thereof was kg·PE/(mmolZr)·h.

As shown in Examples 14–17 in Table 3, in regard to styrene polymerization, the activity of binuclear metallocene catalyst ($P_3$) was increased by about 170% comparing with that of the monometallic catalyst compound (*) of Example 14. As shown in Examples 18–26, in regard to ethylene polymerization, the activities of binuclear metallocene complexs of Examples 21–26 were increased by 108~139% comparing with those of the monometallic catalyst compound ($A_4$) of Examples 18–20.

The present invention can be easily carried out by an ordinary skilled person in the art. Many modifications and changes may be deemed to be within the scope of the present invention as defined in the following claims.

What is claimed is:

1. A metallocene complex for olefin or styrene polymerization prepared by reacting a transition metal complex represented by the general formula (A) and a compound having at least two functional groups represented by the general formulae (B), (C) or (D), having a structure in which ancillary ligands of the transition metal complex are bridged with a functional group of the compound having at least two functional groups:

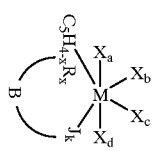
(A)

$$T^1—Y—R^2—Y^1—T^2 \quad (B)$$

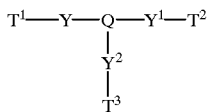
(C)

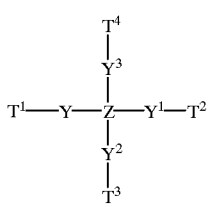
(D)

wherein
M is a transition metal of Group IIIB-VIII of the Periodic Table;
R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;
x is 0, 1, 2, 3 or 4;
B is a covalent bonding group linking ($C_5H_{4-x}R_x$) and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;
J is selected from the group consisting of a cyclopentadienyl group, an alkyl substituted amine group, an aryl substituted amine group, an alkyl substituted phosphine group, an aryl substituted phosphine group, a sulfur atom and an oxygen atom;
k is 0 or 1, and when k is 0, B is a hydrogen atom or a methyl group;

X is selected from the group consisting of a halogen, a triflate, a trifluoroacetate, a hydroxy, an alkyl substituted siloxy, an aryl substituted siloxy, a triphenylphosphine, an alkyl, and an aryl;

a, b, c and d are 0 or 1;

$T^1$, $T^2$, $T^3$ and $T^4$ are selected from the group consisting of H, Na, Li, K, and a magnesium halide;

Y, $Y^1$, $Y^2$ and $Y^3$ are each selected from the group consisting of an oxygen atom, a sulfur atom, an alkyl with or without a double bond or a hetero atom, an aryl with or without a double bond or a hetero atom, a thiirane group

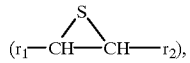

—$Nr_1$ and —$Pr_2$, wherein $r_1$ and $r_2$ are selected from the group consisting of a hydrogen atom, an alkyl group of $C_1$ to $C_{10}$, a cycloalkyl group of $C_1$ to $C_{10}$, an alkoxy group of $C_1$ to $C_{10}$, an aryl group of $C_6$ to $C_{20}$, an alkylaryl group of $C_6$ to $C_{20}$ and an arylalkyl of $C_6$ to $C_{20}$;

$R^2$ is selected from the group consisting of a linear or branched alkyl group of $C_1$ to $C_{20}$; a cycloalkyl group of $C_3$ to $C_{20}$; a substituted cycloalkyl group of $C_3$ to $C_{20}$; an aryl group of $C_6$ to $C_{40}$; and an alkyl group, an aryl group, an alkylaryl group and an arylalkyl group either with or without a double bond or a hetero atom;

Q is a nitrogen atom or —$Cr^3$, wherein $r^3$ is selected from the group consisting of a hydrogen atom, an alkyl group of $C_1$ to $C_{10}$, a cycloalkyl group of $C_1$ to $C_{10}$, an alkoxy group of $C_1$ to $C_{10}$, an aryl group of $C_6$ to $C_{20}$, an alkylaryl group of $C_6$ to $C_{20}$ and an arylalkyl group of $C_6$ to $C_{20}$; and Z is a carbon atom, a silicon atom, a germanium atom or

2. The metallocene complex of claim 1, represented by the general formula (I), which is prepared by reacting said transition metal complex and said compound having two functional groups in the molar ratio of 2:1:

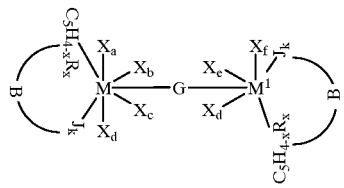

(I)

wherein

M and $M^1$ are each a transition metal of Group IIIB-VIII of the Periodic Table;

R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;

x is 0, 1, 2, 3 or 4;

B is a covalent bonding group linking ($C_5H_{4-x}R_x$) and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group;

X is selected from the group consisting of a halogen, a triflate, a trifluoroacetate, a hydroxy, an alkyl substituted siloxy, an aryl substituted siloxy, a triphenylphosphine, an alkyl, and an aryl;

a, b, c, d, e, and f are 0 or 1; and

G is a bonding group which bonds two transition metal atoms, and is represented as —$YR^2Y^1$—, wherein Y and $Y^1$ are selected from the group consisting of an oxygen atom, a sulfur atom, an alkyl group with or without a double bond or a hetero atom, an aryl group with or without a double bond or a hetero atom, a thiirane group

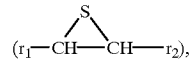

—$Nr_1$ and —$Pr_2$, wherein $r_1$ and $r_2$ are a hydrogen atom, an alkyl group of $C_1$ to $C_{10}$, a cycloalkyl group of $C_{1-10}$, an alkoxy group of $C_{1-10}$, an aryl group of $C_{6-20}$, an alkylaryl group of $C_{6-20}$, or arylalkyl group of $C_{6-20}$.

3. The metallocene complex of claim 1, represented by the general formula (II), which is prepared by reacting said transition metal complex and said compound having two functional groups in the molar ratio of 2:2:

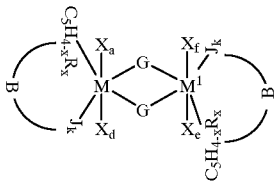

(II)

wherein

M and $M^1$ are each a transition metal of Group IIIB-VIII of the Periodic Table;

R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;

x is 0, 1, 2, 3 or 4;

B is a covalent bonding group linking ($C_5H_{4-x}R_x$) and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group;

X is selected from the group consisting of a halogen, a triflate, a trifluoroacetate, a hydroxy, an alkyl substituted siloxy, an aryl substituted siloxy, a triphenylphosphine, an alkyl, and an aryl;

a, b, e and f are 0 or 1; and

G is a bonding group which bonds two transition metal atoms, and is represented as —YR$^2$Y$^1$—, wherein Y and Y$^1$ are selected from the group consisting of an oxygen atom, a sulfur atom, an alkyl group with or without a double bond or a hetero atom, an aryl group with or without a double bond or a hetero atom, a thiirane group

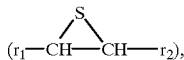

—Nr$_1$ and —Pr$_2$, wherein r$_1$ and r$_2$ are a hydrogen atom, an alkyl group of C$_1$ to C$_{10}$, a cycloalkyl group of C$_{1-10}$, an alkoxy group of C$_{1-10}$, an aryl group of C$_{6-20}$, an alkylaryl group of C$_{6-20}$, or arylalkyl group of C$_{6-20}$.

4. The metallocene complex of claim 1, represented by the general formula (III), which is prepared by reacting said transition metal complex and said compound having two functional groups in the molar ratio of 2:3:

(III)

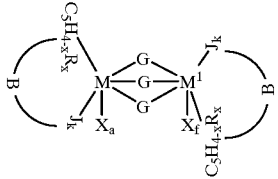

wherein

M and M$^1$ are each a transition metal of Group IIIB-VIII of the Periodic Table;

R is a hydrocarbon group of C$_1$ to C$_{20}$ or a hydrocarbon group of C$_1$ to C$_{20}$ containing a halogen, an amine group, a phosphine group or an alkoxy group, and the two adjacent R groups are bonded to a carbon of a C$_4$ to C$_{20}$ hydrocarbon group to form a polycycliccyclopentadienyl group in the transition metal complex;

x is 0, 1, 2, 3 or 4;

B is a covalent bonding group linking (C$_5$H$_{4-x}$R$_x$) and J$_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group;

X is selected from the group consisting of a halogen, a triflate, a trifluoroacetate, a hydroxy, an alkyl substituted siloxy, an aryl substituted siloxy, a triphenylphosphine, an alkyl, and an aryl;

a, and f are 0 or 1; and

G is a bonding group which bonds two transition metal atoms, and is represented as —YR$^2$Y$^1$—, wherein Y and Y$^1$ are selected from the group consisting of an oxygen atom, a sulfur atom, an alkyl group with or without a double bond or a hetero atom, an aryl group with or without a double bond or a hetero atom, a thiirane group

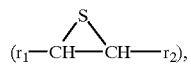

—Nr$_1$ and —Pr$_2$, where r$_1$ and r$_2$ are a hydrogen atom, an alkyl group of C$_1$ to C$_{10}$, a cycloalkyl group of C$_{1-10}$, an alkoxy group of C$_{1-10}$, an aryl group of C$_{6-20}$, an alkylaryl group of C$_{6-20}$, or arylalkyl group of C$_{6-20}$.

5. The metallocene complex of claim 1, represented by the general formula (IV), which is prepared by reacting said transition metal complex and said compound having two functional groups in the molar ratio of 2:4:

(IV)

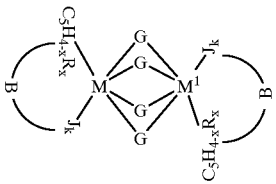

wherein

M and M$^1$ are each a transition metal of Group IIIB-VIII of the Periodic Table;

R is a hydrocarbon group of C$_1$ to C$_{20}$ or a hydrocarbon group of C$_1$ to C$_{20}$ containing a halogen, an amine group, a phosphine group or an alkoxy group, and the two adjacent R groups are bonded to a carbon of a C$_4$ to C$_{20}$ hydrocarbon group to form a polycycliccyclopentadienyl group in the transition metal complex;

x is 0, 1, 2, 3 or 4;

B is a covalent bonding group linking (C$_5$H$_{4-x}$R$_x$) and J$_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group; and

G is a bonding group which bonds two transition metal atoms, and is represented as —YR$^2$Y$^1$—, wherein Y and Y$^1$ are selected from the group consisting of an oxygen atom, a sulfur atom, an alkyl group with or without a double bond or a hetero atom, an aryl group with or without a double bond or a hetero atom, a thiirane group

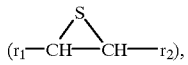

—Nr₁ and —Pr₂, wherein $r_1$ and $r_2$ are a hydrogen atom, an alkyl group of $C_1$ to $C_{10}$, a cycloalkyl group of $C_{1\text{-}10}$, an alkoxy group of $C_{1\text{-}10}$, an aryl group of $C_{6\text{-}20}$, an alkyaryl group of $C_{6\text{-}20}$, or arylalkyl group of $C_{6\text{-}20}$.

6. The metallocene complex of claim 1, represented by the general formula (V), which is prepared by reacting said transition metal complex (A) and said compound (C) having three functional groups in the molar ratio of 3:1:

(V)

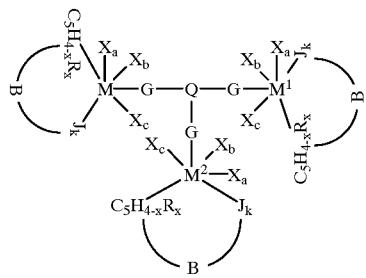

wherein

M, M¹, and M² are each a transition metal of Group IIIB-VIII of the Periodic Table;

R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;

x is 0, 1, 2, 3 or 4;

B is a covalent bonding group linking $(C_5H_{4-x}R_x)$ and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group;

X is selected from the group consisting of a halogen, a triflate, a trifluoroacetate, a hydroxy, an alkyl substituted siloxy, an aryl substituted siloxy, a triphenylphosphine, an alkyl, and an aryl;

a, b, and c are 0 or 1;

G is a bonding group which bonds two transition metal atoms, and is represented as —YR²Y¹—, wherein Y and Y¹ are selected from the group consisting of an oxygen atom, a sulfur atom, an alkyl group with or without a double bond or a hetero atom, an aryl group with or without a double bond or a hetero atom, a thiirane group

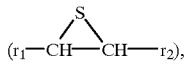

—Nr₁ and —Pr₂, where $r_1$ and $r_2$ are a hydrogen atom, an alkyl group of $C_1$ to $C_{10}$, a cycloalkyl group of $C_{1\text{-}10}$, an alkoxy group of $C_{1\text{-}10}$, an aryl group of $C_{6\text{-}20}$, an alkylaryl group of $C_{6\text{-}20}$, or arylalkyl group of $C_{6\text{-}20}$; and Q is a nitrogen atom or —Cr³, wherein $r^3$ is selected from the group consisting of a hydrogen atom, an alkyl group of $C_1$ to $C_{10}$, a cycloalkyl group of $C_1$ to $C_{10}$, an alkoxy group of $C_1$ to $C_{10}$, an aryl group of $C_6$ to $C_{20}$, an alkylaryl group of $C_6$ to $C_{20}$ and an arylalkyl group of $C_6$ to $C_{20}$.

7. The metallocene complex of claim 1, represented by the general formula (VI), which is prepared by reacting said transition metal complex (A) and said compound (D) having four functional groups in the molar ratio of 4:1:

(VI)

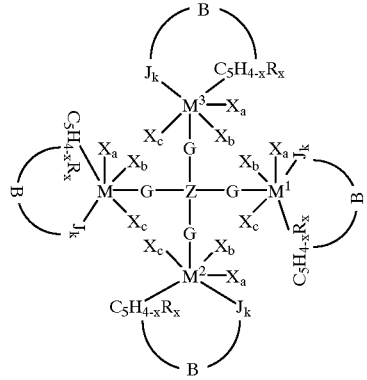

wherein

M, M¹, M², and M³ are each a transition metal of Group IIIB-VIII of the Periodic Table;

R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;

x is 0, 1, 2, 3 or 4;

B is a covalent bonding group linking $(C_5H_{4-x}R_x)$ and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group;

X is selected from the group consisting of a halogen, a triflate, a trifluoroacetate, a hydroxy, an alkyl substituted siloxy, an aryl substituted siloxy, a triphenylphosphine, an alkyl, and an aryl;

a, b, and c are 0 or 1;

G is a bonding group which bonds two transition metal atoms, and is represented as —YR²Y¹—, wherein Y and Y¹ are selected from the group consisting of an oxygen atom, a sulfur atom, an alkyl group with or without a double bond or a hetero atom, an aryl group with or without a double bond or a hetero atom, a thiirane group

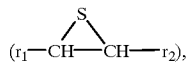

—Nr₁ and —Pr₂, where r₁ and r₂ are a hydrogen atom, an alkyl group of $C_1$ to $C_{10}$, a cycloalkyl group of $C_{1-10}$, an alkoxy group of $C_{1-10}$, an aryl group of $C_{6-20}$, an alkylaryl group of $C_{6-20}$, or arylalkyl group of $C_{6-20}$; and Z is a carbon atom, a silicon atom, a germanium atom or

8. A method of preparing a metallocene complex having a structure in which ancillary ligands of the transition metal complex represented by the general formula (A) are bridged with a functional group of the compounds having at least two functional groups represented by the general formulae (B), (C) and (D), which comprises reacting said transition metal complex with said compounds having at least two functional groups in a solvent:

(A)
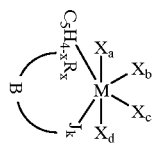

(B)
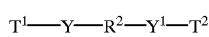

(C)
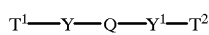

(D)
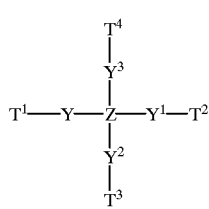

wherein
M is a transition metal of Group IIIB-VIII of the Periodic Table;
R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;

x is 0, 1, 2, 3 or 4;

B is a covalent bonding group linking $(C_5H_{4-x}R_x)$ and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group;

X is selected from the group consisting of a halogen, a triflate, a trifluoroacetate, a hydroxy, an alkyl substituted siloxy, an aryl substituted siloxy, a triphenylphosphine, an alkyl, and an aryl;

a, b, c and d are 0 or 1;

$T^1$, $T^2$, $T^3$ and $T^4$ are selected from the group consisting of H, Na, Li, K, and a magnesium halide;

Y, $Y^1$, $Y^2$ and $Y^3$ are selected from the group consisting of an oxygen atom, a sulfur atom, an alkyl with or without a double bond or a hetero atom, an aryl with or without a double bond or a hetero atom, a thiirane group

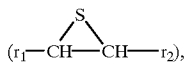

—Nr₁ and —Pr₂, where r₁ and r₂ are selected from the group consisting of a hydrogen atom, an alkyl group of $C_1$ to $C_{10}$, a cycloalkyl group of $C_1$ to $C_{10}$, an alkoxy group of $C_1$ to $C_{10}$, an aryl group of $C_6$ to $C_{20}$, an alkylaryl group of $C_6$ to $C_{20}$ and an arylalkyl of $C_6$ to $C_{20}$;

$R^2$ is selected from the group consisting of a linear or branched alkyl group of $C_1$ to $C_{20}$; a cycloalkyl group of $C_3$ to $C_{20}$; a substituted cycloalkyl group of $C_3$ to $C_{20}$; an aryl group of $C_6$ to $C_{40}$; and an alkyl group, an aryl group, an alkylaryl group and an arylalkyl group either with or without a double bond or a hetero atom;

Q is a nitrogen atom or —Cr³, wherein r³ is selected from the group consisting of a hydrogen atom, an alkyl group of $C_1$ to $C_{10}$, a cycloalkyl group of $C_1$ to $C_{10}$, an alkoxy group of $C_1$ to $C_{10}$, an aryl group of $C_6$ to $C_{20}$, an alkylaryl group of $C_6$ to $C_{20}$ and an arylalkyl group of $C_6$ to $C_{20}$; and Z is a carbon atom, a silicon atom, a germanium atom or

9. The method of claim 8 wherein said metallocene complex is represented by the general formula (I) and wherein said metallocene complex is prepared by reacting said transition metal complex with said compound having two functional groups in the molar ratio of 2:1:

(I)

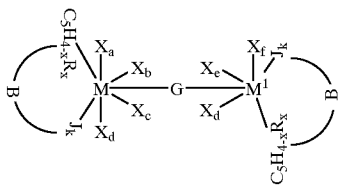

(II)

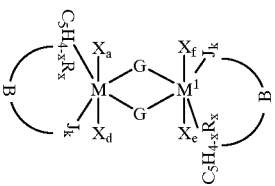

wherein

M and $M^1$ are each a transition metal of Group IIIB-VIII of the Periodic Table;

R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;

x is 0, 1, 2, 3 or 4;

B is a covalent bonding group linking $(C_5H_{4-x}R_x)$ and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group;

X is selected from the group consisting of a halogen, a triflate, a trifluoroacetate, a hydroxy, an alkyl substituted siloxy, an aryl substituted siloxy, a triphenylphosphine, an alkyl, and an aryl;

a, b, c, d, e, and f are 0 or 1; and

G is a bonding group which bonds two transition metal atoms, and is represented as $-YR^2Y^1-$, wherein Y and $Y^1$ are selected from the group consisting of an oxygen atom, a sulfur atom, an alkyl group with or without a double bond or a hetero atom, an aryl group with or without a double bond or a hetero atom, a thiirane group

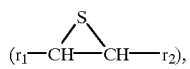

$-Nr_1$ and $-Pr_2$, where $r_1$ and $r_2$ are a hydrogen atom, an alkyl group of $C_1$ to $C_{10}$, a cycloalkyl group of $C_{1-10}$, an alkoxy group of $C_{1-10}$, an aryl group of $C_{6-20}$, an alkylaryl group of $C_{6-20}$, or arylalkyl group of $C_{6-20}$.

10. The method of claim 8 wherein said metallocene complex is represented by the general formula (II) and wherein said metallocene complex is prepared by reacting said transition metal complex with said compound having two functional groups in the molar ratio of 2:2:

wherein

M and $M^1$ are each a transition metal of Group IIIB-VIII of the Periodic Table;

R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;

x is 0 1, 2, 3 or 4;

B is a covalent bonding group linking $(C_5H_{4-x}R_x)$ and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group;

X is selected from the group consisting of a halogen, a triflate, a trifluoroacetate, a hydroxy, an alkyl substituted siloxy, an aryl substituted siloxy, a triphenylphosphine, an alkyl, and an aryl;

a, b, e and f are 0 or 1; and

G is a bonding group which bonds two transition metal atoms, and is represented as $-YR^2Y^1-$, wherein Y and $Y^1$ are selected from the group consisting of an oxygen atom, a sulfur atom, an alkyl group with or without a double bond or a hetero atom, an aryl group with or without a double bond or a hetero atom, a thiirane group

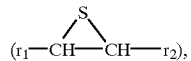

$-Nr_1$ and $-Pr_2$, wherein $r_1$ and $r_2$ are a hydrogen atom, an alkyl group of $C_1$ to $C_{10}$, a cycloalkyl group of $C_{1-10}$, an alkoxy group of $C_{1-10}$, an aryl group of $C_{6-20}$, an alkylaryl group of $C_{6-20}$, or arylalkyl group of $C_{6-20}$.

11. The method of claim 8 wherein said metallocene complex is represented by the general formula (III) and wherein said metallocene complex is prepared by reacting said transition metal complex with said compound having two functional groups in the molar ratio of 2:3:

(III)

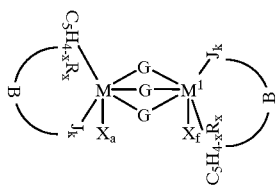

(IV)

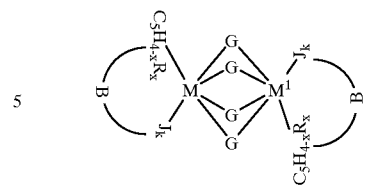

wherein

M and M¹ are each a transition metal of Group IIIB-VIII of the Periodic Table;

R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;

x is 0, 1, 2, 3 or 4;

B is a covalent bonding group linking $(C_5H_{4-x}R_x)$ and $J_k$, which is selected from the group consisting of dialkyl silicon, alkyl aryl silicon, diaryl silicon, dialkyl germanium, alkyl aryl germanium, diaryl geranium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group;

X is selected from the group consisting of a halogen, a triflate, a trifluoroacetate, a hydroxy, an alkyl substituted siloxy, an aryl substituted siloxy, a triphenylphosphine, an alkyl, and an aryl;

a, and f are 0 or 1; and

G is a bonding group which bonds two transition metal atoms, and is represented as $-YR^2Y^1-$, wherein Y and $Y^1$ are selected from the group consisting of an oxygen atom, a sulfur atom, an alkyl group with or without a double bond or a hetero atom, an aryl group with or without a double bond or a hetero atom, a thiirane group

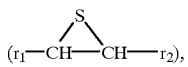

$-Nr_1$ and $-Pr_2$, wherein $r_1$ and $r_2$ are a hydrogen atom, an alkyl group of $C_1$ to $C_{10}$, a cycloalkyl group of $C_{1-10}$, an alkoxy group of $C_{1-10}$, an aryl group of $C_{6-20}$, an alkylaryl group of $C_{6-20}$, or arylalkyl group of $C_{6-20}$.

12. The method of claim 8 wherein said metallocene complex is represented by the general formula (IV) and wherein said metallocene complex is prepared by reacting said transition metal complex with said compound having two functional groups in the molar ratio of 2:4:

wherein

M and M¹ are each a transition metal of Group IIIB-VIII of the Periodic Table;

R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;

x is 0, 1, 2, 3 or 4;

B is a covalent bonding group linking $(C_5H_{4-x}R_x)$ and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group; and

G is a bonding group which bonds two transition metal atoms, and is represented as $-YR^2Y^1-$, wherein Y and $Y^1$ are selected from the group consisting of an oxygen atom, a sulfur atom, an alkyl group with or without a double bond or a hetero atom, an aryl group with or without a double bond or a hetero atom, a thiirane group

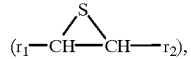

$-Nr_1$ and $-Pr_2$, wherein $r_1$ and $r_2$ are a hydrogen atom, an alkyl group of $C_1$ to $C_{10}$, a cycloalkyl group of $C_{1-10}$, an alkoxy group of $C_{1-10}$, an aryl group of $C_{6-20}$, an alkylaryl group of $C_{6-20}$, or arylalkyl group of $C_{6-20}$.

13. The method of claim 8 wherein said metallocene complex is represented by the general formula (V) and wherein said metallocene complex is prepared by reacting said transition metal complex (A) and said compound (C) having three functional groups in the molar ratio of 3:1:

(V)

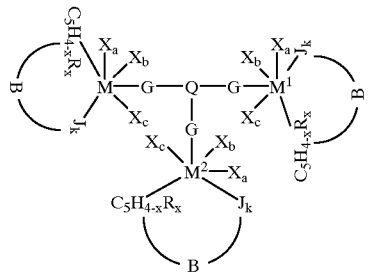

wherein

M, M¹, and M² are each a transition metal of Group IIIB-VIII of the Periodic Table;

R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;

x is 0, 1, 2, 3 or 4;

B is a covalent bonding group linking $(C_5H_{4-x}R_x)$ and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group;

X is selected from the group consisting of a halogen, a triflate, a trifluoroacetate, a hydroxy, an alkyl substituted siloxy, an aryl substituted siloxy, a triphenylphosphine, an alkyl, and an aryl;

a, b, and c are 0 or 1;

G is a bonding group which bonds two transition metal atoms, and is represented as $—YR^2Y^1—$, wherein Y and $Y^1$ are selected from the group consisting of an oxygen atom, a sulfur atom, an alkyl group with or without a double bond or a hetero atom, an aryl group with or without a double bond or a hetero atom, a thiirane group

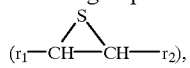

$—Nr_1$ and $—Pr_2$, where $r_1$ and $r_2$ are a hydrogen atom, an alkyl group of $C_1$ to $C_{10}$, a cycloalkyl group of $C_{1-10}$, an alkoxy group of $C_{1-10}$, an aryl group of $C_{6-20}$, an alkylaryl group of $C_{6-20}$, or arylalkyl group of $C_{6-20}$; and Q is a nitrogen atom or $—Cr^3$, wherein $r^3$ is selected from the group consisting of a hydrogen atom, an alkyl group of $C_1$ to $C_{10}$, a cycloalkyl group of $C_1$ to $C_{10}$, an alkoxy group of $C_1$ to $C_{10}$, an aryl group of $C_6$ to $C_{20}$, an alkylaryl group of $C_6$ to $C_{20}$ and an arylalkyl group of $C_6$ to $C_{20}$.

14. The method of claim 8 wherein said metallocene complex is represented by the general formula (VI) and wherein said metallocene complex is prepared by reacting said transition metal complex (A) with said compound (D) having three functional groups in the molar ratio of 4:1:

(VI)

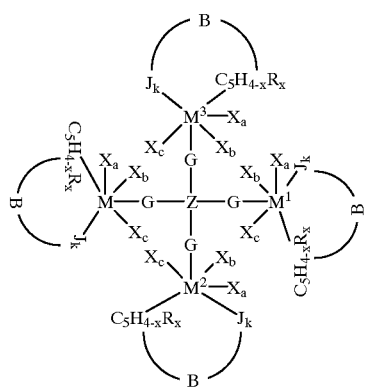

wherein

M, $M^1$, $M^2$, and $M^3$ are each a transition metal of Group IIIB-VIII of the Periodic Table;

R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;

x is 0, 1, 2, 3 or 4;

B is a covalent bonding group linking $(C_5H_{4-x}R_x)$ and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;

J is selected from the group consisting of a cyclopentadienyl group, an alkyl substituted amine group, an aryl substituted amine group, an alkyl substituted phosphine group, an aryl substituted phosphine group, a sulfur atom and an oxygen atom;

k is 0 or 1, and when k is 0, B is a hydrogen atom or a methyl group;

X is selected from the group consisting of a halogen, a triflate, a trifluoroacetate, a hydroxy, an alkyl substituted siloxy, an aryl substituted siloxy, a triphenylphosphine, an alkyl, and an aryl;

a, b, and c are 0 or 1;

G is a bonding group which bonds two transition metal atoms, and is represented as $—YR^2Y^1—$, wherein Y and $Y^1$ are selected from the group consisting of an oxygen atom, a sulfur atom, an alkyl group with or without a double bond or a hetero atom, an aryl group with or without a double bond or a hetero atom, a thiirane group

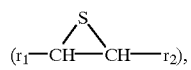

$—Nr_1$ and $—Pr_2$, wherein $r_1$ and $r_2$ are a hydrogen atom, an alkyl group of $C_1$ to $C_{10}$, a cycloalkyl group of $C_{1-10}$, an alkoxy group of $C_{1-10}$, an aryl group of $C_{6-20}$, an alkylaryl group of $C_{6-20}$, or arylalkyl group of $C_{6-20}$; and Z is a carbon atom, a silicon atom, a germanium atom or

15. A method of preparing a metallocene complex having a structure in which ancillary ligands of the transition metal complex represented by the general formula (A) are bridged with a dianion, a trianion or a tetraanion compound which comprises reacting said transition metal complex with said dianion, trianion or tetraanion compound wherein said anion compound is prepared by reacting a compound having a hydroxyl group, a thiol group, a primary amine group, a secondary amine group, a primary phosphorous group or a secondary phosphorous group with an alkali metal compound:

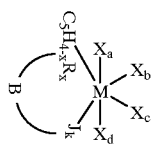
(A)

wherein
- M is a transition metal of Group IIIB-VIII of the Periodic Table;
- R is a hydrocarbon group of $C_1$ to $C_{20}$ or a hydrocarbon group of $C_1$ to $C_{20}$ containing a halogen, an amine group, a phosphine group or an alkoxy group, and the two adjacent R groups are bonded to a carbon of a $C_4$ to $C_{20}$ hydrocarbon group to form a polycycliccyclopentadienyl group in the transition metal complex;
- x is 0, 1, 2, 3 or 4;
- B is a covalent bonding group linking ($C_5H_{4-x}R_x$) and $J_k$, which is selected from the group consisting of dialkyl silicon, alkyl aryl silicon, diaryl silicon, dialkyl germanium, alkyl aryl germanium, diaryl germanium, alkyl phosphine, aryl phosphine, amine, methylene, and ethylene;
- J is selected from the group consisting of a cyclopentadienyl group, an alkyl substituted amine group, an aryl substituted amine group, an alkyl substituted phosphine group, an aryl substituted phosphine group, a sulfur atom and an oxygen atom;
- k is 0 or 1, and when k is 0, B is a hydrogen atom or a methyl group;
- X is selected from the group consisting of a halogen, a triflate, a trifluoroacetate, a hydroxy, an alkyl substituted siloxy, an aryl substituted siloxy, a triphenylphosphine, an alkyl, and an aryl; and
- a, b, c and d are 0 or 1.

16. The method of claim 8 wherein said reaction is carried out at the temperature of about −78° C. to about 118° C.

17. The method of claim 8 wherein said solvent is selected from the group consisting of toluene, dichloromethane, hexane, heptane, THF, benzene, ether, xylene, chloroform and mesitylene.

18. The metallocene complex of claims 1, 2, 3, 4, 5, 6, or 7, wherein the transition metal of Group IIIB-VIII is selected from the group consisting of Ti, Zr, Hf, Ta, Ni, Rh, and Ir.

19. The method of claims 8, 9, 10, 11, 12, 13, 14, 15, 16, or 17, wherein the transition metal of Group IIIB-VIII is selected from the group consisting of Ti, Zr, Hf, Ta, Ni, Rh, and Ir.

* * * * *